US008102416B2

(12) United States Patent
Ito et al.

(10) Patent No.: US 8,102,416 B2
(45) Date of Patent: Jan. 24, 2012

(54) MEDICAL APPARATUS

(75) Inventors: Seiichi Ito, Hachioji (JP); Junichi Onishi, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/023,806

(22) Filed: Feb. 9, 2011

(65) Prior Publication Data
US 2011/0234780 A1    Sep. 29, 2011

Related U.S. Application Data

(63) Continuation of application No. PCT/JP2010/065324, filed on Sep. 7, 2010.

(30) Foreign Application Priority Data

Feb. 22, 2010  (JP) ................................. 2010-036480

(51) Int. Cl.
*A61B 5/05*    (2006.01)
*A62B 1/04*    (2006.01)
(52) U.S. Cl. .......................................... 348/65; 600/424
(58) Field of Classification Search ........... 348/65, 348/72, 77; 382/128; 434/262; 600/424, 600/423, 372
See application file for complete search history.

(56) References Cited

U.S. PATENT DOCUMENTS

| | | | | |
|---|---|---|---|---|
| 5,840,024 A | * | 11/1998 | Taniguchi et al. | 600/424 |
| 7,835,785 B2 | * | 11/2010 | Scully et al. | 600/424 |
| 7,940,967 B2 | * | 5/2011 | Ozaki et al. | 382/128 |
| 2005/0020878 A1 | | 1/2005 | Ohnishi et al. | |
| 2005/0272971 A1 | | 12/2005 | Ohnishi et al. | |
| 2009/0130642 A1 | * | 5/2009 | Tada et al. | 434/262 |
| 2009/0161927 A1 | | 6/2009 | Mori et al. | |

FOREIGN PATENT DOCUMENTS

| | | |
|---|---|---|
| JP | 2002-119507 | 4/2002 |
| JP | 2002-306403 | 10/2002 |
| JP | 2004-089483 | 3/2004 |
| JP | 2004-105725 | 4/2004 |
| JP | 2009-056143 | 3/2009 |
| JP | 2009-056238 | 3/2009 |
| JP | 2009-056239 | 3/2009 |
| WO | WO 2004/010857 A1 | 2/2004 |
| WO | WO 2004/023986 A1 | 3/2004 |
| WO | WO 2007/129493 A1 | 11/2007 |

\* cited by examiner

*Primary Examiner* — Gims Philippe
(74) *Attorney, Agent, or Firm* — Scully, Scott, Murphy & Presser, P.C.

(57) ABSTRACT

A medical apparatus includes an endoscopic insertion portion provided with an image pickup unit and a channel; a treatment unit provided with a sensor and a bending portion and passed through a channel, with a distal end portion of the treatment unit being allowed to protrude from an insertion-portion distal end portion of the endoscopic insertion portion, where the sensor is disposed in the distal end portion and the bending portion is adapted to bend the distal end portion; a storage unit adapted to store three-dimensional image data; a target position setting unit adapted to set the target position based on the three-dimensional image data; a virtual endoscopic image generating unit adapted to generate a virtual endoscopic image using a line-of-sight parameter which includes a position, a direction, and a roll angle of the distal end portion detected by the sensor, based on the three-dimensional image data; and an image processing unit adapted to perform a superimposition process and thereby display operation information used to insert the distal end portion to the target position in superimposition on the virtual endoscopic image.

13 Claims, 21 Drawing Sheets

FIG.17
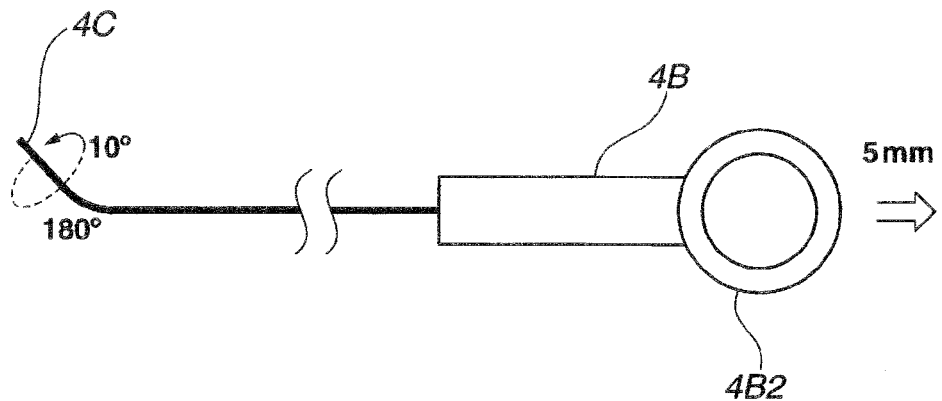
FIG.18A
ROTATE XX DEGREES CLOCKWISE
FIG.18B
PRESS ROTATION UP BUTTON
FIG.18C
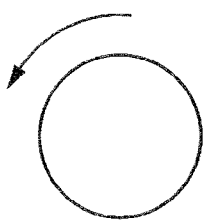
FIG.18D
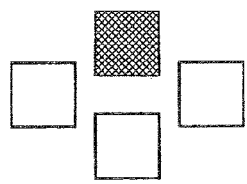

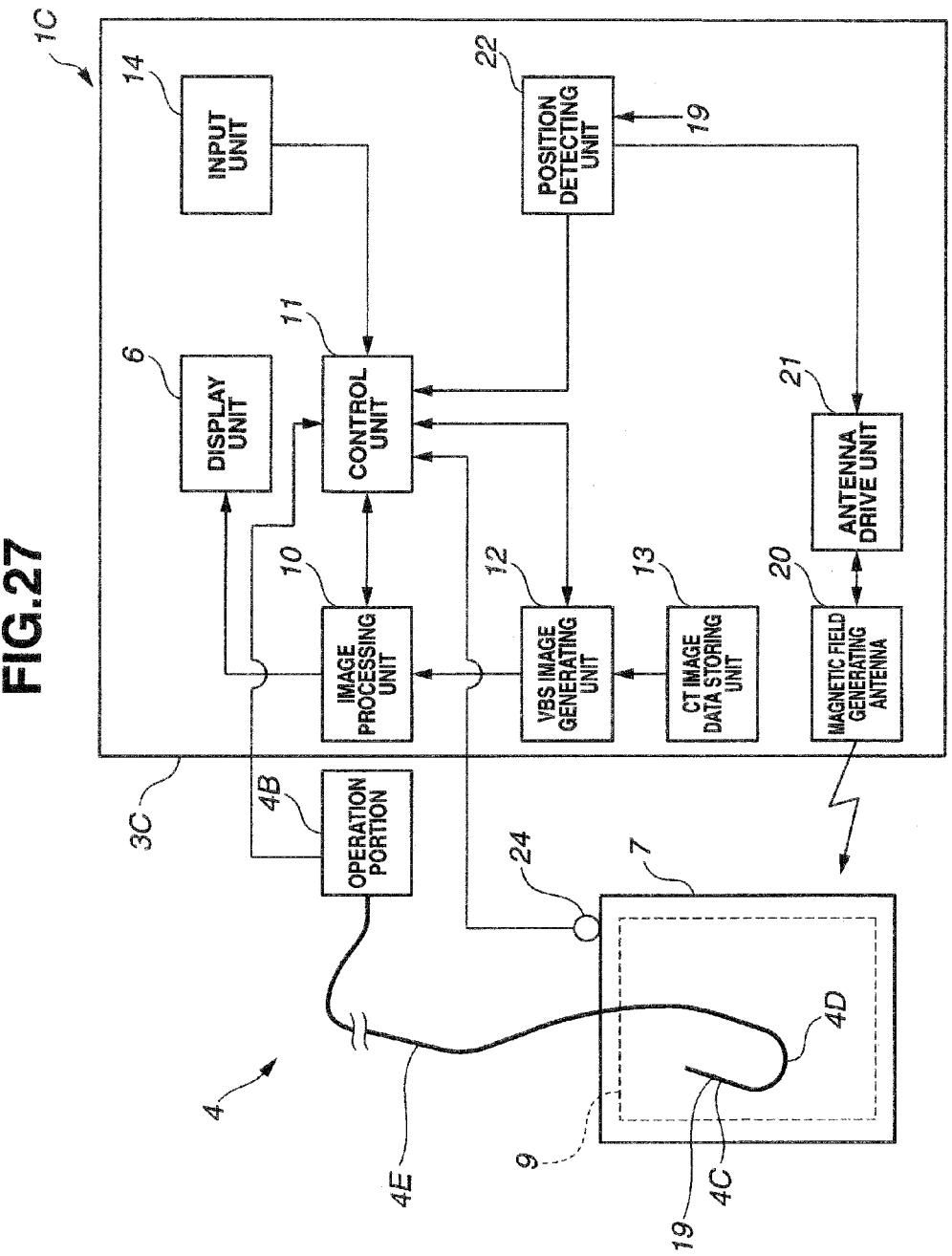

US 8,102,416 B2

MEDICAL APPARATUS

CROSS REFERENCE TO RELATED PATENT APPLICATION

This application is a continuation application of PCT/JP2010/065324 filed on Sep. 7, 2010 and claims benefit of Japanese Application No. 2010-036480 filed in Japan on Feb. 22, 2010, the entire contents of which are incorporated herein by this reference.

BACKGROUND OF THE INVENTION

1. Field of the Invention

The present invention relates to a medical apparatus equipped with a treatment instrument to be inserted into a lumen of a subject to carry out treatment, and more particularly to a medical apparatus which aids a treatment instrument insertion operation using virtual endoscopic images based on three-dimensional image data of the lumen.

2. Description of the Related Art

In recent years, diagnosis and treatment have come to be carried out widely using three-dimensional image data. For example, three-dimensional images inside a subject are obtained by picking up tomograms of the subject using an X-ray CT (Computed Tomography) apparatus and used to carry out diagnosis and the like of a target site.

The CT apparatus performs successive scans (helical scans) of the subject continually while rotating X-ray irradiation position and detection position continuously by moving the subject. Then, three-dimensional image data is obtained from a large number of successive two-dimensional tomograms of the subject.

Examples of the three-dimensional image data used for diagnosis and treatment include three-dimensional image data of the bronchi of the lungs. The three-dimensional image data of the bronchi of the lungs is used, for example, to three-dimensionally locate an abnormal site where lung cancer is suspected. Then, to check the abnormal site by a biopsy, an endoscope is inserted into the bronchi, a treatment instrument such as a biopsy needle or biopsy forceps is protruded from a distal end portion of the endoscope, and a sample is taken from the target site.

In a lumen having a plurality of bifurcations, such as a bronchus, it is sometimes not easy to insert a treatment instrument precisely into a target site in the lung in a short time. Thus, for example, Japanese Patent Application Laid-Open Publication No. 2009-56238 discloses a navigation system which forms three-dimensional images of a lumen based on three-dimensional image data of the subject, determines a route to a target spot along the lumen using the three-dimensional images, further forms and displays virtual endoscopic images of the lumen along the route, and thereby guides insertion operation.

Also, to assist insertion operation, Japanese Patent Application Laid-Open Publication No. 2002-119507 discloses a medical apparatus which displays a virtual image viewed from a distal end portion of a catheter inserted in a subject while Japanese Patent Application Laid-Open Publication No. 2002-306403 discloses an endoscope apparatus which displays a virtual image of a distal end portion of an endoscope in superimposition on a virtual endoscopic image.

SUMMARY OF THE INVENTION

According to one aspect of the present invention, there is provided a medical apparatus comprising: an endoscopic insertion portion provided with an image pickup unit and a channel which passes through an inner part; a treatment unit provided with a sensor and a bending portion and passed through a channel, with a distal end portion of the treatment unit being allowed to protrude from an insertion-portion distal end portion of the endoscopic insertion portion, where the sensor is disposed in the distal end portion and configured to detect a position, a direction, and a roll angle and the bending portion is adapted to bend the distal end portion; a storage unit adapted to store three-dimensional image data of the lumen of a subject acquired in advance; a target position setting unit adapted to set the target position based on the three-dimensional image data; a virtual endoscopic image generating unit adapted to generate a virtual endoscopic image using a line-of-sight parameter which includes the position, the direction, and the roll angle of the distal end portion detected by the sensor, based on the three-dimensional image data; and an image processing unit adapted to perform a superimposition process and thereby display operation information used to insert the distal end portion to the target position in superimposition on the virtual endoscopic image.

BRIEF DESCRIPTION OF THE DRAWINGS

FIG. 17 is a diagram showing an example of manipulations of the medical apparatus according to the first embodiment;

FIG. 18A is a diagram showing an example of the display of operation information about the medical apparatus according to the first embodiment;

FIG. 18B is a diagram showing an example of the display of operation information about the medical apparatus according to the first embodiment;

FIG. 18C is a diagram showing an example of the display of operation information about the medical apparatus according to the first embodiment;

FIG. 18D is a diagram showing an example of the display of operation information about the medical apparatus according to the first embodiment;

FIG. 27 is a configuration diagram for illustrating a configuration of a medical apparatus according to a third embodiment.

DETAILED DESCRIPTION OF THE PREFERRED EMBODIMENTS

First Embodiment

Figure 1:
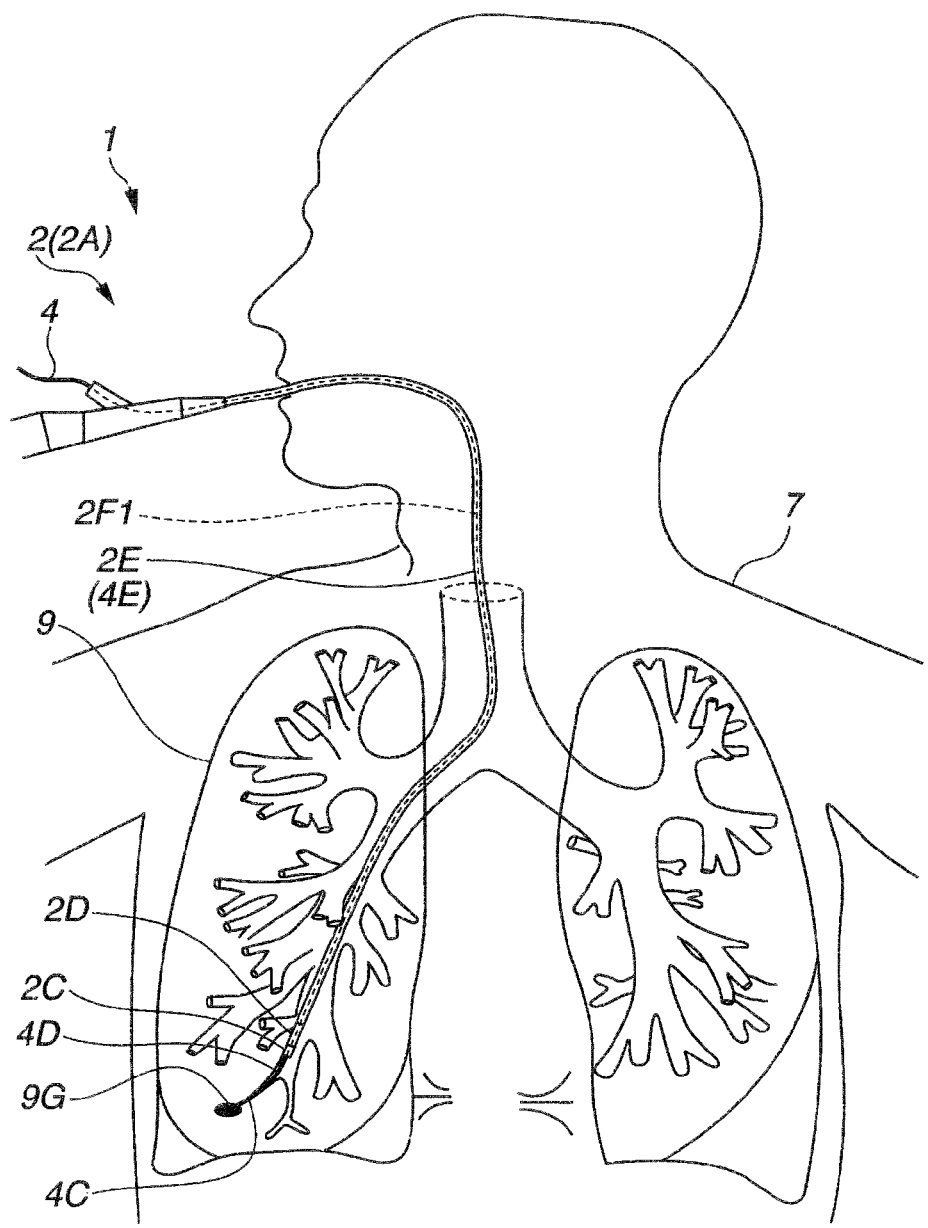
FIG. 1 is a schematic diagram for illustrating insertion of an endoscope into a bronchus using a medical apparatus according to a first embodiment.

A medical apparatus 1 according to a first embodiment of the present invention will be described below with reference to the drawings. FIG. 1 is a schematic diagram showing how a target site 9G at a bronchial end is biopsied by passing an insertion portion 4E of a treatment instrument 4 through a channel 2F1 of an endoscope 2A of an endoscope apparatus 2 inserted into a bronchus 9 of a patient 7.

As shown in FIG. 1, the bronchi 9 have multiple bifurcations. Therefore, to insert the treatment instrument 4 to the target site 9G, a surgeon needs to make a correct selection judgment and perform a proper insertion operation at each bifurcation based on an endoscopic image picked up by a CCD 2G (see FIG. 2) which is image pickup means in an insertion-portion distal end portion 2C of the endoscope 2A. Incidentally, a CMOS or the like may be used as the image pickup means.

Figure 2:
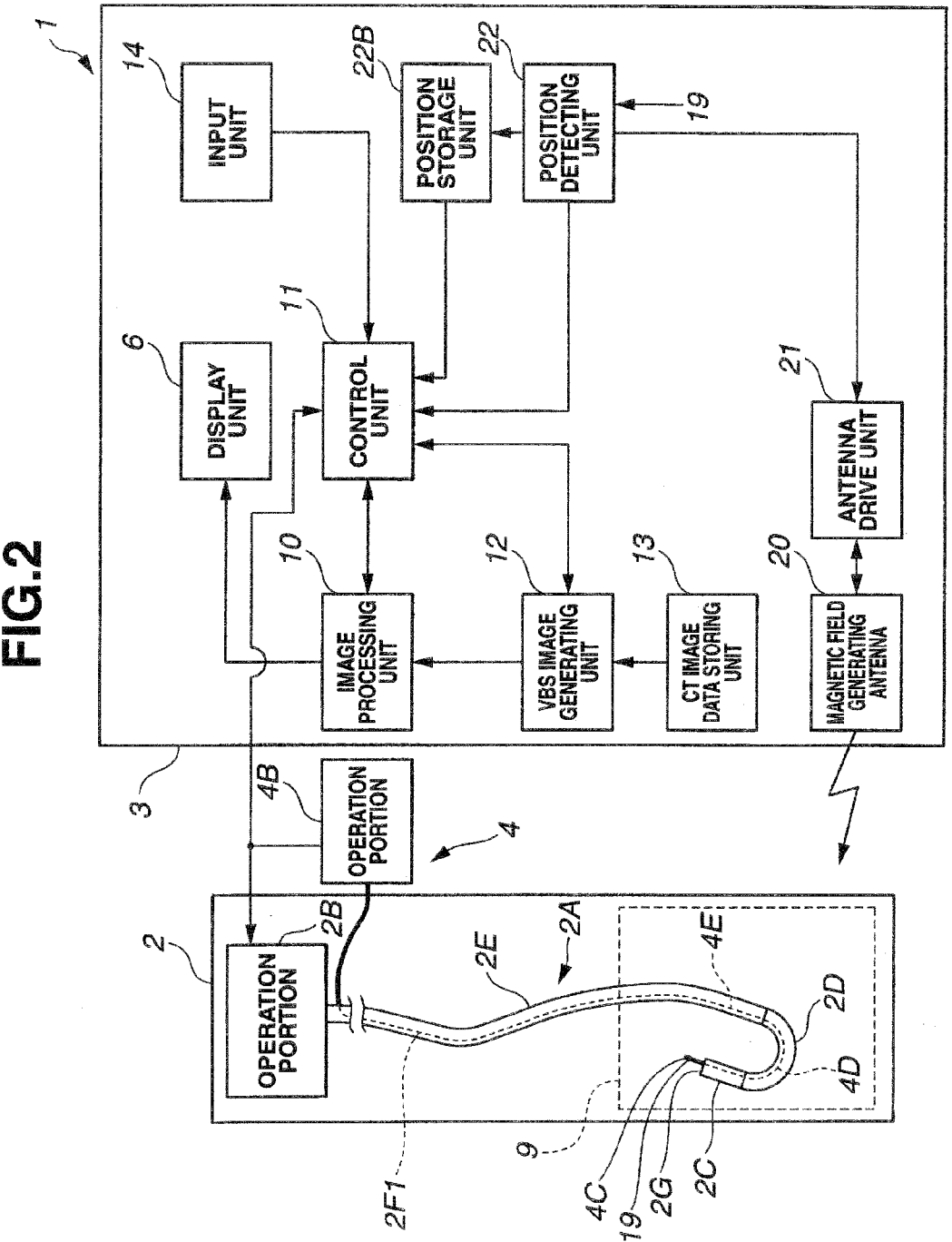
FIG. 2 is a configuration diagram for illustrating a configuration of the medical apparatus according to the first embodiment.

As shown in FIG. 2, in addition to the endoscope apparatus 2 and the treatment instrument 4, the medical apparatus 1 includes an insertion aid apparatus 3 adapted to aid the surgeon in making judgments and performing operations. That is, a first function of the insertion aid apparatus 3 is to help the surgeon make selection judgments at bifurcations. A second function of the insertion aid apparatus 3 is to help the surgeon perform bending operation.

The endoscope apparatus 2 includes the insertion-portion distal end portion 2C, a bending portion 2D used for bending operation of the insertion-portion distal end portion 2C, an insertion portion 2E elongated in shape, and an operation portion 2B (see FIG. 2), which are installed consecutively. Meanwhile, the treatment instrument 4 serving as treatment means includes a distal end portion 4C, a bending portion 4D used for bending operation of the distal end portion 4C, an insertion portion 4E elongated in shape, and an operation portion 4B (see FIG. 2), which are installed consecutively.

As shown in FIG. 2, the insertion aid apparatus 3 includes a CT image data storing unit 13, an input unit 14, a virtual endoscopic image generating unit 12 serving as virtual endoscopic image generating means (hereinafter the virtual endoscopic image will also be referred to as a "VBS image" which stands for Virtual Bronchus Scope image), an image processing unit 10, a display unit 6, a sensor 19 disposed in the distal end portion 4C of the treatment instrument 4, a magnetic field generating antenna 20, an antenna drive unit 21, a position detecting unit 22, a position storage unit 22B, and a control unit 11 which performs overall control. Incidentally, the components of the insertion aid apparatus 3 may be common with components (not shown) of the endoscope apparatus 2 which perform various processes.

The CT image data storing unit 13 serving as storage means is a semiconductor storage device, a magnetic recording device, or the like which stores three-dimensional image data, for example, in DICOM (Digital Imaging and Communication in Medicine) format by receiving the three-dimensional image data via a receiving unit (not shown) as the three-dimensional image data is generated by a known CT apparatus (not shown) which picks up X-ray tomograms of the patient 7.

The input unit 14 includes a keyboard, a mouse, and the like used by the surgeon to input information to the medical apparatus 1. In setting the position of the target site 9G based on three-dimensional image data, the surgeon also uses the input unit 14 serving as target position setting means.

The VBS image generating unit 12 generates VBS images from the three-dimensional image data in DICOM format based on a six-dimensional line-of-sight parameter described later.

The image processing unit 10 serving as image processing means performs image processing on endoscopic images (hereinafter also referred to as "real images") picked up by the CCD 2G as well as performs processing to display operation information, rotating operation information about the bending portion 4D, and a VBS image in superimposition as described later, where the operation information, the rotating operation information, and the VBS image are used to help insert the distal end portion 4C to the target site 9G. The display unit 6 serves as display means which displays real images, VBS images, and the like.

As described earlier, the treatment instrument 4 has the sensor 19 in the distal end portion 4C to detect a position, a direction, and a roll angle (hereinafter also referred to as the "position and the like"). The sensor 19 is, for example, a magnetic field detection sensor and is adapted to detect a magnetic field generated by the magnetic field generating antenna 20 made up of three antennas disposed outside the patient 7 and thereby detect position and the like where the treatment instrument 4 is disposed. Alternatively, an MR sensor, a Hall element, a coil, or the like may be used as the magnetic field detection sensor.

For example, ac magnetic fields of different frequencies are generated from multiple antennas of the magnetic field generating antenna 20 by the antenna drive unit 21. The sensor 19 detects the multiple ac magnetic fields of different frequencies in distinction from one another, allowing the position detecting unit 22 to detect information about the position, direction, and roll angle (X, Y, Z, a, e, r) of the sensor 19 with respect to the magnetic field generating antenna 20 based on information from the sensor 19, where (X, Y, Z) are three-dimensional coordinate values, (a) is an azimuth angle, (e) is an elevation angle, and (r) is a roll angle. Since the position of disposition of the sensor 19 in the distal end portion 4C is known, a predetermined location of the treatment instrument 4, e.g., position of a distal end 4H is calculated based on the position of the sensor 19. The position storage unit 22B time-sequentially stores the position of the distal end 4H and the like detected by the position detecting unit 22.

Figure 3:
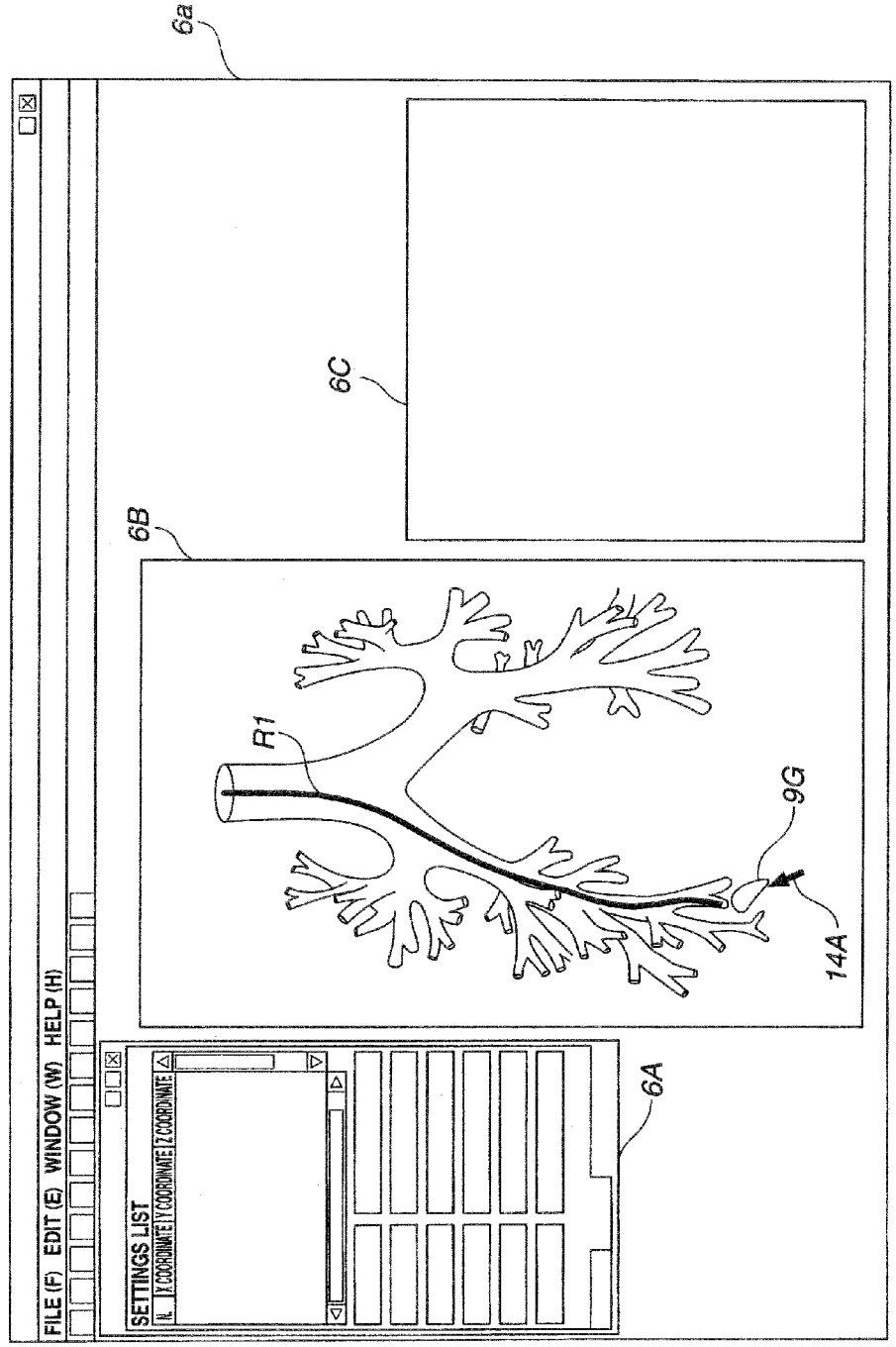
FIG. 3 is a diagram showing an example of a display screen of the medical apparatus according to the first embodiment.

Next, a method for insertion operation aid in the medical apparatus 1 will be described. As shown in FIG. 3, when the insertion aid apparatus 3 performs insertion navigation, first a display screen 6a of the display unit 6 displays information 6A including information about the patient 7 and information about bifurcations of the bronchi 9, a virtual image 6B of the bronchi 9 based on three-dimensional image data, and a VBS image B (6C) and the like whose details are not illustrated. The VBS image B is a VBS image based on the line-of-sight parameter of the CCD 2G. The line-of-sight parameter is a six-dimensional parameter which includes the position, direction, and roll angle (X, Y, Z, a, e, r). Incidentally, as described later, a VBS image A is a VBS image based on the line-of-sight parameter of the distal end portion 4C of the treatment instrument 4.

By operating the input unit 14, the surgeon sets target site 9G of the lungs, which is a target position, with a pointer 14A or the like using the virtual image 6B. Incidentally, the surgeon may set any site such as a passing point along the way rather than the target site 9G. Once the target site 9G or the like is set, the insertion aid apparatus 3 calculates an insertion route R1, and displays the insertion route R1 in superimposition on the virtual image 6B as shown in FIG. 3. The insertion route R1 is a core line leading to the target site 9G out of core lines which link center-of-gravity points or center points of lumen cross sections of the virtual endoscopic images.

Then, the VBS image generating unit 12 creates a VBS image B for each of the multiple bifurcations along the insertion route R1. Incidentally, the insertion aid apparatus 3 may have a VBS image storage unit (not shown) adapted to store VBS images of the bronchi 9 generated beforehand by the VBS image generating unit 12, and may display VBS images of the bifurcations along the insertion route R1 by extracting them from the stored VBS images.

Figure 4:
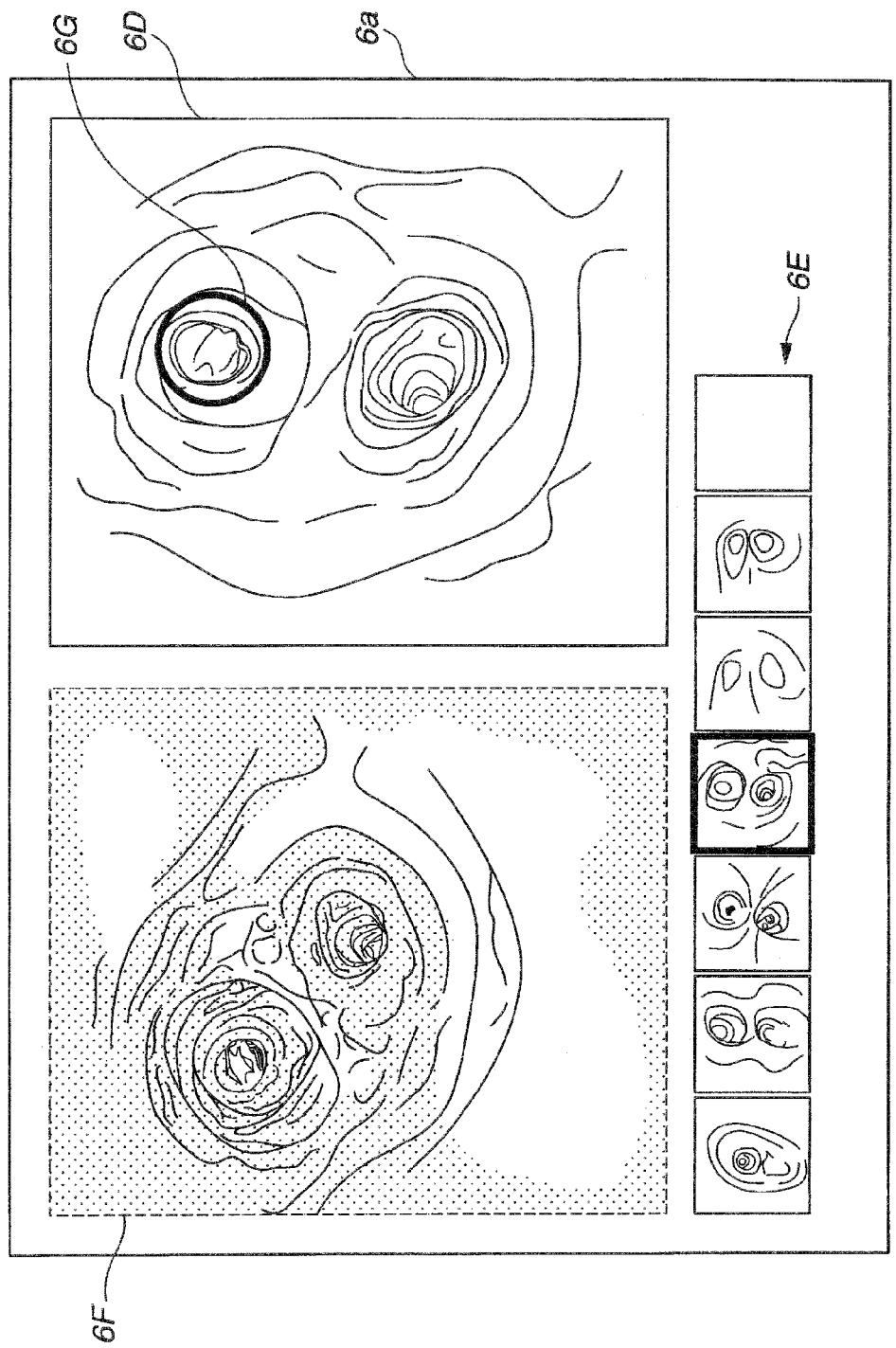
FIG. 4 is a diagram showing an example of the display screen of the medical apparatus according to the first embodiment.

Then, once an insertion operation is started, as shown in FIG. 4, the display screen 6a displays a real image 6F picked up by the CCD 2G and processed by the image processing unit 10, multiple thumbnail VBS images (6E) which are reduced VBS images of the bifurcations appearing in the course of the insertion operation, and a VBS image B (6D) of the bifurcation which will appear next. The VBS image B (6D) is superimposed with guiding information 6G indicating which of the lumens located ahead of the bifurcation to insert the distal end portion into. By performing the insertion operation while making selection judgments based on the guiding information 6G of the insertion aid apparatus 3, the surgeon can insert the insertion-portion distal end portion 2C to near the target site 9G. So doing, the treatment instrument 4 does not need to be passed through the channel 2F1 in the insertion portion 2E. Alternatively, the treatment instrument 4 may be passed through the channel 2F1 of the insertion portion 2E with the distal end portion 4C fixed to a predetermined position of the insertion-portion distal end portion 2C of the insertion portion 2E.

If the target site 9G is at an ending of the bronchus 9, the surgeon cannot insert the insertion-portion distal end portion 2C of the endoscope 2A to the target site 9G even if the insertion portion 2E of the endoscope 2A has a thin diameter. Thus, next the surgeon has to insert the distal end portion 4C of the treatment instrument 4 into the target site 9G in a deeper part by protruding the treatment instrument 4 from a treatment instrument outlet 2F of the insertion-portion distal end portion 2C of the endoscope 2A and carry out predetermined treatment there.

That is, in order to be able to be inserted into a thin lumen, the insertion portion 2E of the endoscope 2A has a diameter of, for example, 3 mm, which is smaller than a gastrointestinal endoscope or the like, but the treatment instrument 4 has a diameter of, for example, 1 mm so as to be able to be inserted into a still thinner peripheral lumen. Therefore, the bending portion 4D of the treatment instrument 4 is bendable only either in an up/down direction or a left/right direction. That is, unlike gastrointestinal endoscopes, the bending portion 4D cannot be bend freely in all four directions: left, right, up, and down. Consequently, the bending operation of the bending portion 4D requires skills. Incidentally, although the phrase "up/down direction or left/right direction" is used for the sake of convenience, the phrase means one direction in a plane orthogonal to an insertion direction.

Furthermore, in a thin-diameter lumen into which the insertion portion 2E of the endoscope 2A cannot be inserted, the surgeon cannot view bifurcations using real images from the CCD 2G.

However, the VBS image generating unit 12 of the insertion aid apparatus 3 generates the VBS image A based on the line-of-sight parameter of the distal end portion 4C, more precisely, part of the distal end portion 4C, for example, the distal end 4H, of the treatment instrument 4.

Figure 5A:
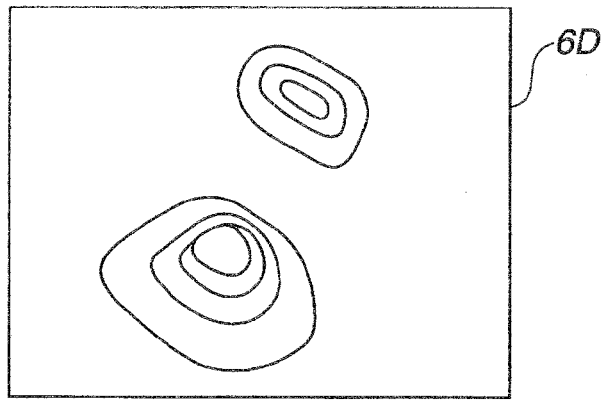
FIG. 5A is a diagram for illustrating a configuration of the display screen of the medical apparatus according to the first embodiment.
Figure 5B:
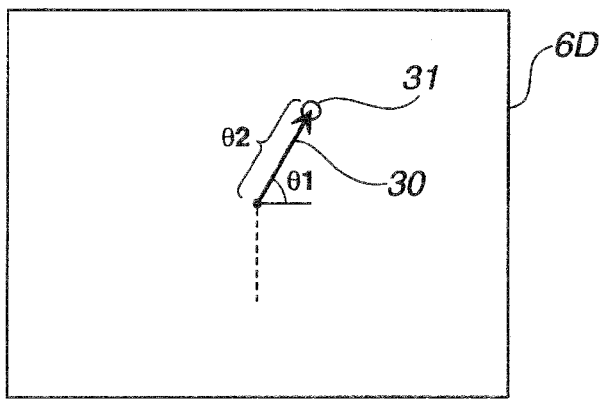
FIG. 5B is a diagram for illustrating the configuration of the display screen of the medical apparatus according to the first embodiment.
Figure 5C:
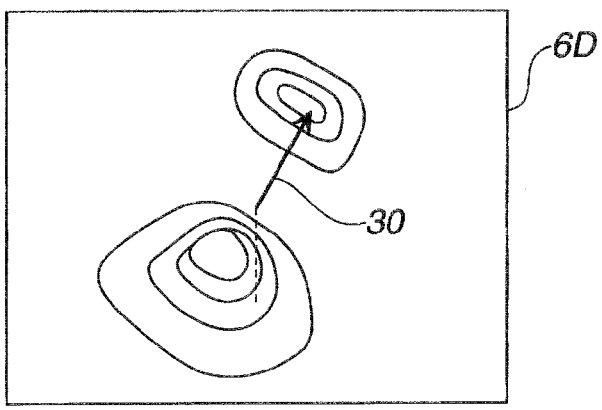
FIG. 5C is a diagram for illustrating the configuration of the display screen of the medical apparatus according to the first embodiment.

That is, as described earlier, the treatment instrument 4 includes the sensor 19 adapted to detect the position and the like. Consequently, the VBS image generating unit 12 generates the VBS image A based on the line-of-sight parameter, which in turn is based on the position and the like detected by the sensor 19, and displays the VBS image A in the display unit 6. Furthermore, the image processing unit 10 causes the display unit 6 to display an image (FIG. 5C) resulting from a superimposition process in which the VBS image A (FIG. 5A) is superimposed with a graphically displayed operations guide image 30 (FIG. 5B) intended to direct the distal end portion to a lumen 31 into which it should be inserted. As shown in FIG. 5B, the graphically displayed operations guide image 30, which is displayed as an arrow, for example, is not simply an image which indicates an insertion direction. That is, direction of the arrow represents a roll angle $\theta 1$ and length of the arrow represents a bending angle $\theta 2$. Incidentally, digital information may be displayed in addition to the graphic display.

Figure 6A:
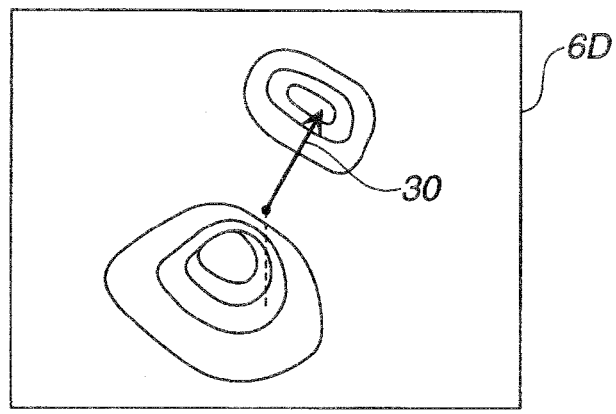
FIG. 6A is a diagram showing an example of the display screen of the medical apparatus according to the first embodiment.
Figure 6B:
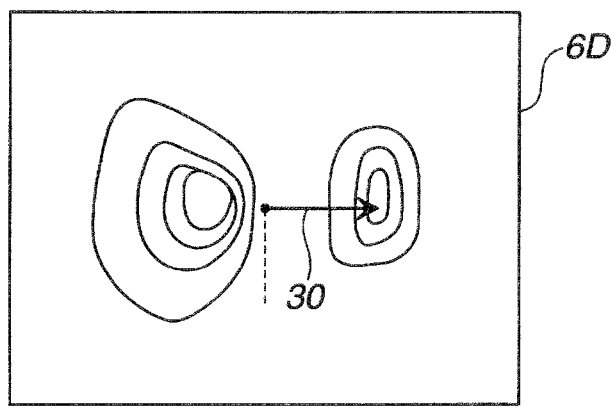
FIG. 6B is a diagram showing an example of the display screen of the medical apparatus according to the first embodiment.
Figure 6C:
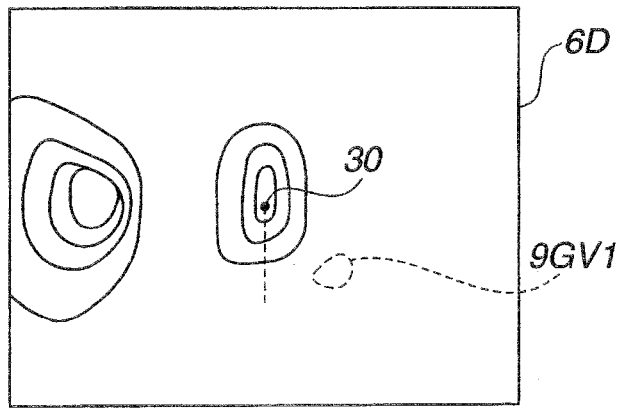
FIG. 6C is a diagram showing an example of the display screen of the medical apparatus according to the first embodiment.

As shown in FIG. 6A, by watching the VBS image A superimposed with the intuitively understandable graphically displayed operations guide image 30 instead of numerals, the surgeon can operate the operation portion 4B and perform a rotating operation. Then, by rotating the treatment instrument 4 by a roll angle $\theta 1$ as shown in FIG. 6B and then by bending the bending portion 4D by a bending angle $\theta 2$ as shown in FIG. 6C using the operation portion 4B, the surgeon can easily orient the distal end portion 4C to a lumen in the direction of the target site 9G. Incidentally, in the rotating operation, the surgeon rotates the bending portion 4D and the distal end portion 4C via the insertion portion 4E by griping and rotating the treatment instrument 4 on the side of a proximal end portion.

That is, even if the treatment instrument 4 is not equipped with a CCD 2G, the insertion aid apparatus 3 allows the surgeon to bring the distal end portion 4C to the target site 9G by watching the VBS image A and making selection judgments at bifurcations based on the guiding information of the VBS image A. Furthermore, even if the bending portion 4D cannot be bend freely in all four directions, the insertion aid apparatus 3 allows the surgeon to operate the bending portion 4D easily based on the operation information displayed by being superimposed on the VBS image A.

Figure 7A:
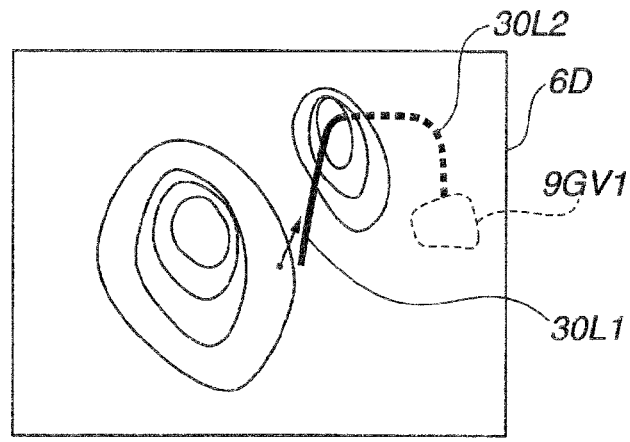
FIG. 7A is a diagram showing an example of the display screen of the medical apparatus according to the first embodiment.
Figure 7B:
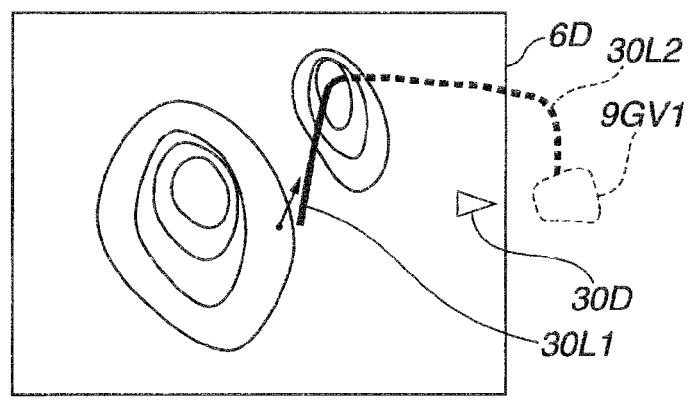
FIG. 7B is a diagram showing an example of the display screen of the medical apparatus according to the first embodiment.

The image processing unit 10 may perform a superimposition process and thereby display an insertion route 30L1 used to insert the distal end portion 4C to the target site 9G in superimposition on the VBS image A. FIG. 7A shows a case in which a transparent image 9GV1 of the target site 90 exists in a screen, where an insertion route 30L2 represented by a broken line is a non-visible insertion route which cannot be seen directly from the position of the distal end portion 4C. On the other hand, FIG. 7B shows a case in which no transparent image 9GV1 of the target site 9G exists in the screen of the VBS image A. However, an arrow 30D indicates the direction in which the target site 9G exists, allowing the surgeon to recognize the direction in which the target site 9G exists. Incidentally, for the sake of explanation, FIG. 7B also illustrates something offscreen that is not displayed in the screen of the VBS image A.

Regarding operation information on the bending portion 4D, the insertion aid apparatus 3 performs a superimposition process and thereby displays the VBS image superimposed with insertion routes, the insertion route 30L1 visible from the position of the distal end portion 4C and the non-visible insertion route 30L2, to the target site 9G from the position of the distal end portion 4C which is being inserted. Thus, being capable of conveying to the surgeon not only the nearest operation information, but also information about subsequent insertion operations, the insertion aid apparatus 3 provides excellent operability.

As described above, with the medical apparatus 1, by performing insertion operation while operating the bending portion 4D according to the operation information displayed in the display unit 6 of the insertion aid apparatus 3, the surgeon can insert the distal end portion 4C precisely to the target site 9G in a short time. Also, since the medical apparatus 1 does not use X-rays, the patient does not get exposed to radiation.

Incidentally, FIG. 6C and the like show an example in which the image processing unit 10 performs a superimposition process and thereby displays the VBS image A in superimposition with the transparent image 9GV1 of the target site 9G. The target site 9G displayed here is located in such a position as not to be viewable using the currently set line-of-sight parameter, but displayed as the transparent image 9GV1 to provide position information about the target site 9G to the surgeon. When displayed, preferably the transparent image 9GV1 is represented by a broken line or displayed in a distinctive color so as to be easily distinguished from viewable sites. Furthermore, by attaching information of a predetermined size to the transparent image 9GV1, information about distance from the target site 9G can be provided to the surgeon using graphic display.

Figure 8A:
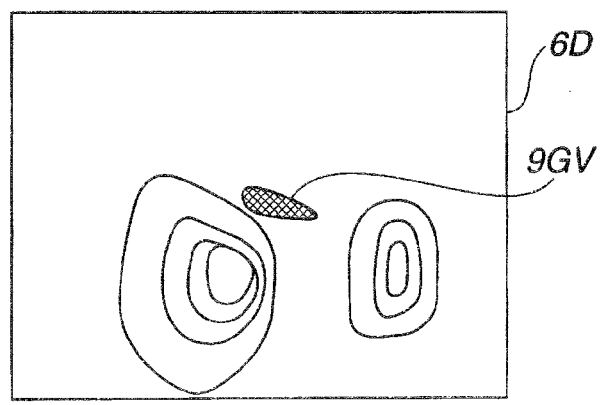
FIG. 8A is a diagram showing an example of the display screen of the medical apparatus according to the first embodiment.
Figure 8B:
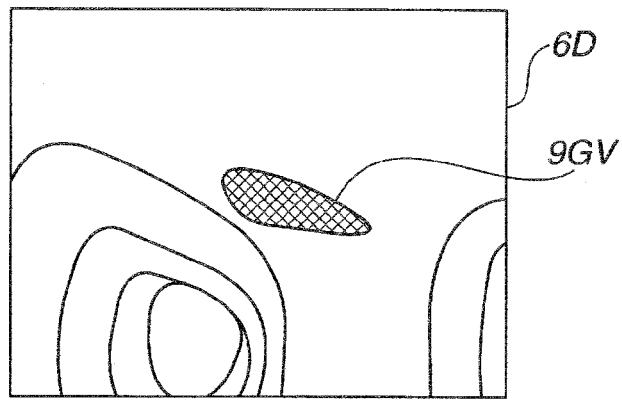
FIG. 8B is a diagram showing an example of the display screen of the medical apparatus according to the first embodiment.
Figure 8C:
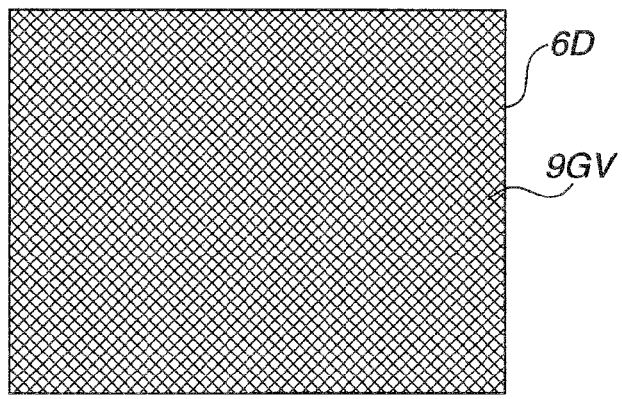
FIG. 8C is a diagram showing an example of the display screen of the medical apparatus according to the first embodiment.

For example, after the distal end 4H is inserted to a position where the target site 9G can be processed, i.e., where the target site 9G is viewable as shown in FIG. 8A, when the distal end 4H further approaches the target site 9G as shown in FIG. 8B, size of an image 9GV of the target site 9G in the VBS image A becomes larger. Then as shown in FIG. 8C, when the distal end portion 4C abuts the target site 9G, the entire VBS image A turns into the image 9GV of the target site 9G. In so doing, to distinguish the target site 9G displayed in the display unit 6 from any other luminal wall abutted by the distal end portion 4C, preferably the image 9GV of the target site 9G is set to be colored or hatched particularly conspicuously.

Figure 9A:
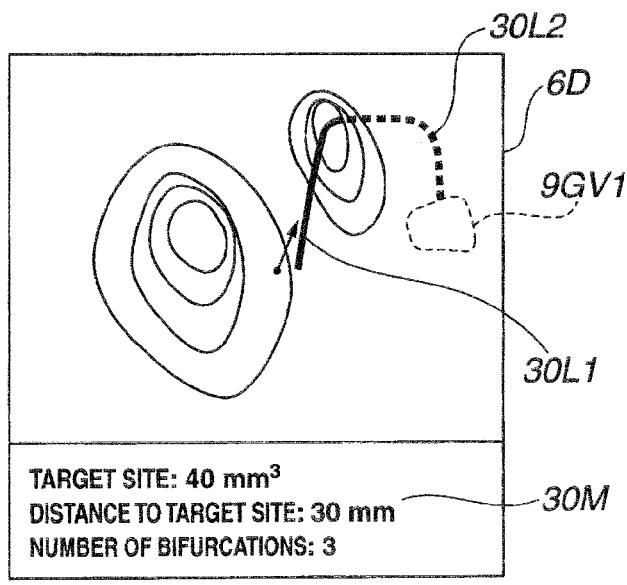
FIG. 9A is a diagram showing an example of the display screen of the medical apparatus according to the first embodiment.
Figure 9B:
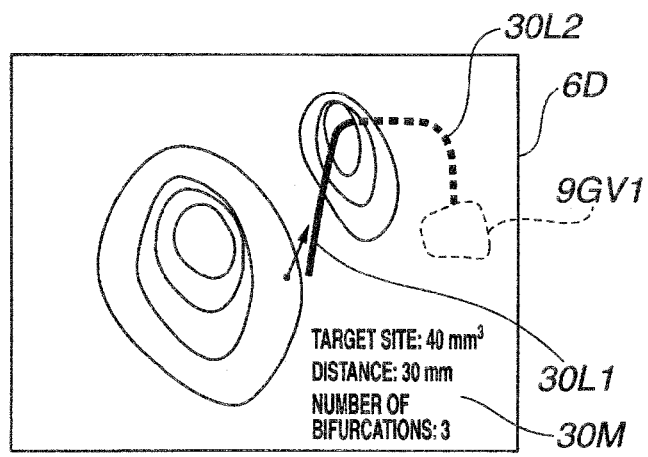
FIG. 9B is a diagram showing an example of the display screen of the medical apparatus according to the first embodiment.

The information of a predetermined size to be attached to the transparent image 9GV1 may have a fixed size to provide intuitive information about the distance from the target site 9G to the surgeon. Preferably, however, the surgeon is allowed to set a predetermined size for a target position i.e., to set the volume of the target site 9G, via the input unit 14. As shown in FIGS. 9A and 9B, when the volume of the target site 9G is set, the image processing unit 10 can perform a superimposition process and thereby display the volume of the target site 9G, length of the insertion route from the current position of the distal end portion 4C to the target site 9G, and the number of bifurcations N on the insertion route in superimposition. Incidentally, FIG. 9A is an example in which operation information is displayed below the VBS image A in superimposition while FIG. 9B is an example in which operation information is displayed in the VBS image A in superimposition. The insertion aid apparatus described above can convey more information to the surgeon, and thus provides more excellent operability. That is, although three-dimensional display such as the virtual image 6B in FIG. 3 is not provided, the surgeon can obtain information about approximate distance to the target site 9G.

Incidentally, the image processing unit 10 may perform a superimposition process of operation information only when bending operation or rotating operation is necessary. That is, when the distal end portion 4C is passing through a non-bifurcated lumen before reaching a bifurcation or when the distal end portion 4C is oriented in a correct insertion direction, there is no need to provide operation information to the surgeon. Thus, preferably the image processing unit 10 performs a superimposition process for display of operation information only when the distal end portion 4C reaches a predetermined operation information display area and a predetermined bending angle threshold and a predetermined roll angle threshold are reached.

Also, preferably the image processing unit 10 displays operation information in superimposition only for bending operation or rotating operation whichever needs to be performed. That is, the image processing unit 10 performs a superimposition process of the operation information when at least either of bending operation and rotating operation is required.

The image processing unit 10 which displays operation information in superimposition based on the bending angle threshold and the roll angle threshold provides good operability because unnecessary information is not presented to the surgeon.

Figure 10A:
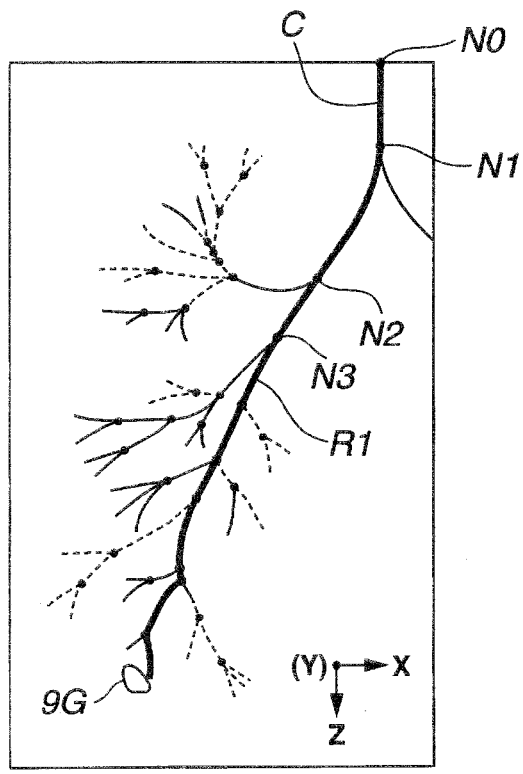
FIG. 10A is an explanatory diagram for illustrating an insertion route of the medical apparatus according to the first embodiment.
Figure 10B:
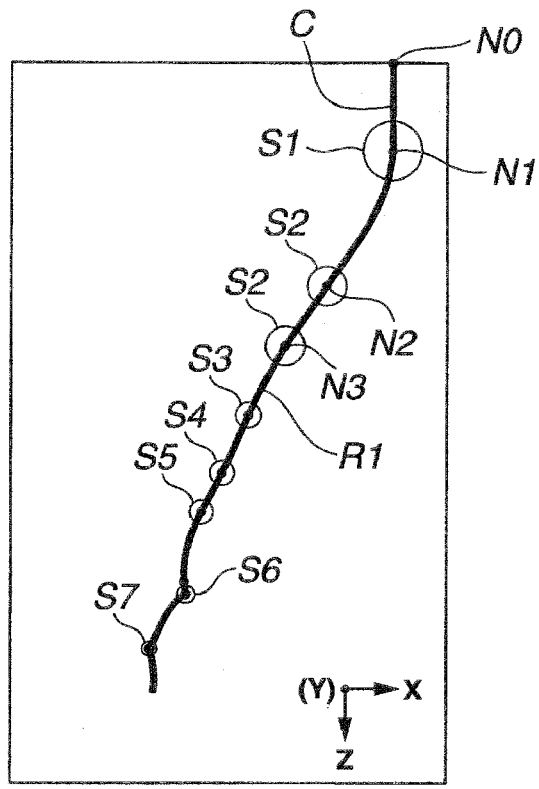
FIG. 10B is an explanatory diagram for illustrating an insertion route of the medical apparatus according to the first embodiment.

As shown in FIGS. 10A and 10B, the operation information display area is a region of the bronchi in a predetermined three-dimensional space with reference to bifurcations N1 to NX of the insertion route R1, for example, in a sphere SX of a predetermined radius from the bifurcation NX. That is, as described later, even after the distal end portion 4C passes a bifurcation, preferably operation information is displayed as long as the distal end portion 4C is located in the operation information display area. This is to display a recovery method or the like in case the distal end portion 4C is inserted into a lumen in a wrong direction due to misoperation or the like, as described later. As described earlier, the position of the distal end portion 4C is calculated based on the position of the sensor 19. Preferably the radius of the sphere SX which provides the operation information display area is equal to or longer than a device tip length L, but may vary with the position of the bifurcation N, where the device tip length L is the length of the bending portion 4D used for bending operation of the distal end portion 4C.

Figure 11:
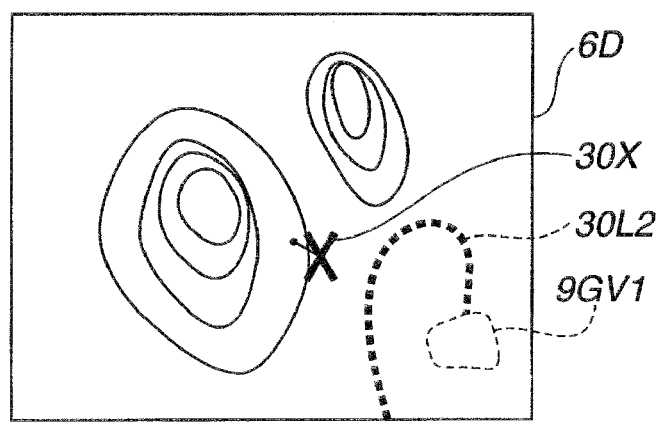
FIG. 11 is a diagram showing an example of the display screen of the medical apparatus according to the first embodiment.

That is, when the distal end portion 4C is located in a lumen off the insertion route due to a wrong operation, the surgeon needs to pull back the distal end portion 4C toward the side of the proximal end portion. In such a case, the image processing unit 10 of the insertion aid apparatus 3 can alert the surgeon by presenting a special display, for example, by displaying an X mark such as shown in FIG. 11 in addition to the superimposed display of the insertion route.

Next, a brief description will be given of a method used by the control unit 11 to calculate the bending angle $\theta 2$ and roll angle $\theta 1$ which are pieces of operation information.

Figure 12:
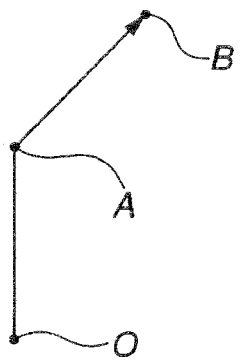
FIG. 12 is a diagram showing vectors of a bending portion of the medical apparatus according to the first embodiment.

Hereinafter, as shown in FIG. 12, the position of the distal end 4H will be defined as point B, a fulcrum for bending of the bending portion 4D as point A, and a starting point of the bending portion 4D on the side of the proximal end portion as point O. The insertion aid apparatus 3 calculates positions of point A, point B, and point O based on time-series data on the position of the distal end 4H stored in the position storage unit 22B.

Figure 13A:
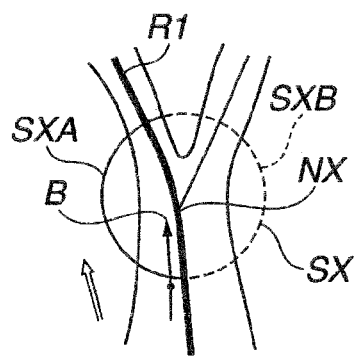
FIG. 13A is a diagram showing an example of movement and the display screen of the medical apparatus according to the first embodiment.
Figure 13B:
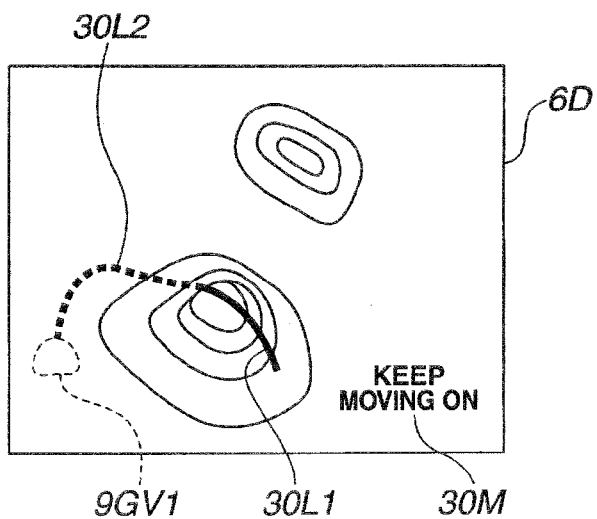
FIG. 13B is a diagram showing an example of the movement and display screen of the medical apparatus according to the first embodiment.

As shown in FIG. 13A, when point B exists in the operation information display area of the bifurcation NX, i.e., in an area SXA of the sphere SX on the side of the insertion route direction, if the distal end portion 4C is kept moving forward, i.e., if the distal end portion 4C is pushed in, the distal end portion 4C can be advanced to a lumen located in the direction along the insertion route R1. Thus, the image processing unit 10 does not display the bending angle $\theta 2$ and the roll angle $\theta 1$ as operation information. That is, as described earlier, when the bending angle $\theta 2$ or the roll angle $\theta 1$ is not higher than its predetermined threshold, the image processing unit 10 does not perform a superimposition process of the bending angle $\theta 2$ or the roll angle $\theta 1$. Incidentally, as shown in FIG. 13B, information that the distal end portion 4C is oriented in the correct insertion direction may be displayed as text information 30M.

Figure 14A:
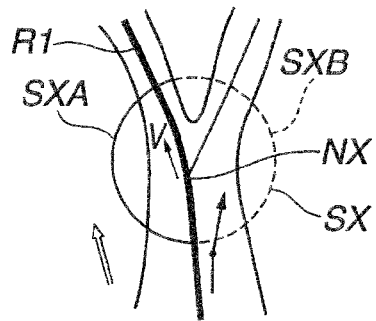
FIG. 14A is a diagram showing an example of movement, operation angle calculation, and the display screen of the medical apparatus according to the first embodiment.
Figure 14B:
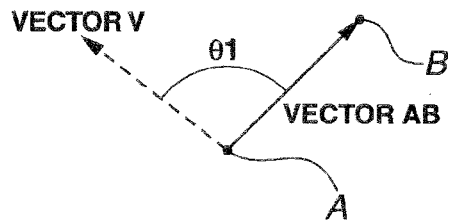
FIG. 14B is a diagram showing an example of the movement, operation angle calculation, and display screen of the medical apparatus according to the first embodiment.

On the other hand, as shown in FIG. 14A, when the distal end 4H (point B) does not exist in the area SXA on the side of the insertion route direction (exists in an area XSB), the distal end portion 4C will advance to a wrong lumen rather than the insertion route R1 if kept moving forward. In this case, the roll angle $\theta 1$ is calculated first. That is, a vector V is derived from a tangent to the insertion direction at a bifurcation of the insertion route, to begin with. Next, a vector AB is derived from position information about point A and point B or from a distal end direction vector at point A. Then, a vector OA is derived and a plane OAV perpendicular to the vector OA is defined. An angle between the vector V and the vector AB which use the vector OA as a reference point, i.e., an angle between the vector V and vector AB projected onto the plane OAV, is the roll angle $\theta 1$ as shown in FIG. 14B.

Figure 14C:
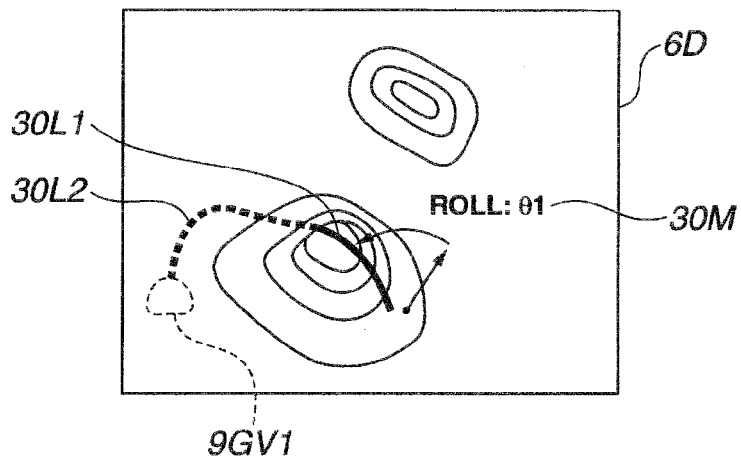
FIG. 14C is a diagram showing an example of the movement, operation angle calculation, and display screen of the medical apparatus according to the first embodiment.

If the distal end 4H (point B) moves to the area on the side of the insertion route direction when the surgeon manipulates the roll angle $\theta 1$, there is no need to calculate the bending angle $\theta 2$. Consequently, only the roll angle $\theta 1$ is displayed in superimposition as shown in FIG. 14C.

Figure 15A:
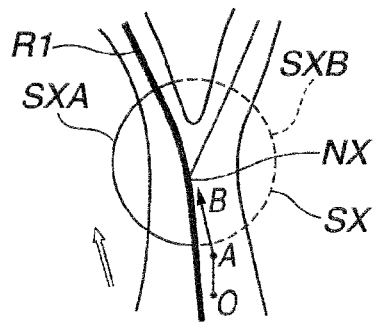
FIG. 15A is a diagram showing an example of the movement, operation angle calculation, and display screen of the medical apparatus according to the first embodiment.
Figure 15B:
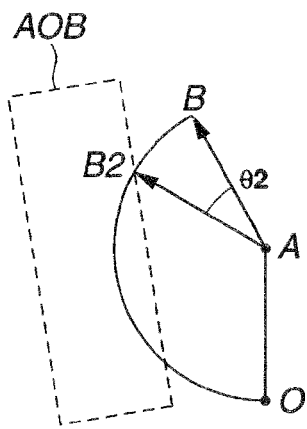
FIG. 15B is a diagram showing an example of the movement, operation angle calculation, and display screen of the medical apparatus according to the first embodiment.
Figure 15C:
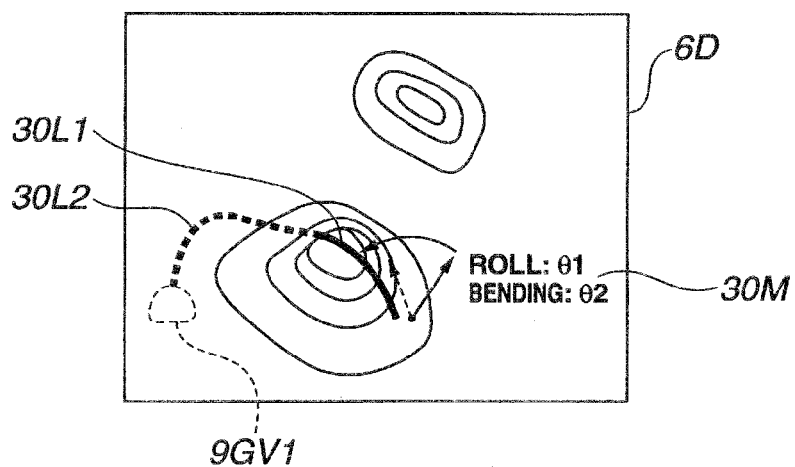
FIG. 15C is a diagram showing an example of the movement, operation angle calculation, and display screen of the medical apparatus according to the first embodiment.

On the other hand, as shown in FIG. 15A, if the distal end 4H (point B) does not move to the area on the side of the insertion route direction when the roll angle $\theta 1$ is manipulated, the bending angle $\theta 2$ is calculated. That is, a circle centered at point A and having a radius equal to the device tip length L is created such that a point of intersection with the area in the insertion route direction on a plane OAB will be point B2. Then, as shown in FIG. 15B, an angle between the vector AB and a vector AB2 is the bending angle $\theta 2$. Consequently, as shown in FIG. 15C, the roll angle $\theta 1$ and the bending angle $\theta 2$ are displayed by being superimposed on the VBS image A.

Figure 16:
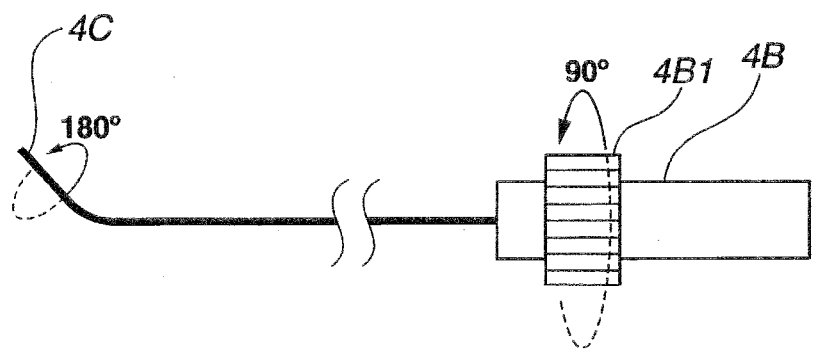
FIG. 16 is a diagram showing an example of manipulations of the medical apparatus according to the first embodiment.

Incidentally, depending on the endoscope 2A or the treatment instrument 4, there are cases in which manipulations of the operation portion 4B on the side of the proximal end portion do not correspond directly to movements of the distal end portion 4C. For example, as shown in FIG. 16, when a rotating portion 4B2 of the operation portion 4B is rotated 360 degrees, the distal end portion 4C might rotate 180 degrees. In such a case, a roll angle θ1 of the rotating portion 4B2 is calculated from the roll angle θ1 of the distal end portion 4C using the calculation formula Θ1=f(θ1). The calculation formula is given, for example, by Θ1=2×θ1. Similarly, a bending angle θ2 of the operation portion 4B is calculated from the bending angle θ2 of the distal end portion using a calculation formula.

Also, as shown in FIG. 17, when the surgeon moves a lever portion 4B2 of the operation portion 4B forward or backward, the distal end portion 4C might rotate or the bending portion might bend. In such a case, an amount of movement of the lever portion 4B2 is calculated from the roll angle θ1 of the distal end portion 4C using the calculation formula Θ1=f1(θ1). For example, if the distal end portion 4C rotates 10 degrees when the lever portion 4B2 is moved 5 mm, the calculation formula used is ΘL=(θ2)/2 (mm). Thus, in this case, operation information about the bending angle or the roll angle is displayed in terms of an amount of lever operation, which is a physical quantity suitable for operation of the surgeon, rather than in degrees.

Furthermore, operating direction is displayed to inform the surgeon of rotating direction or bending direction. The operation information may be displayed either in text form as shown in FIGS. 18A and 18B or in graphic form shown in FIGS. 18C and 18D. The graphic display shown in FIG. 18(C) and the like is superimposed on a virtual endoscopic image.

In the example described above, the second function of the insertion aid apparatus 3 is to aid the bending operation of the bending portion 4D of the treatment instrument 4, but the second function can also be used to aid the bending operation of the bending portion 2D of the endoscope 2A. That is, during insertion operation of the insertion portion 2E, if the distal end portion 4C of the treatment instrument 4 is inserted into the channel 2F1 in advance, the sensor 19 can be placed in a predetermined position of the insertion-portion distal end portion 2C.

Consequently, even if the bending portion 2D of the endoscope 2A can be bended to any one of the up/down direction and left/right direction, the insertion aid apparatus 3 can graphically display bending operation information about the bending portion 2D in superimposition on the VBA image B to the surgeon. Incidentally, the insertion aid apparatus 3 may be configured to perform a process to display the bending operation information in superimposition on a real image.

Also, a virtual image of the treatment instrument 4 may be displayed in the display unit 6, being superimposed on a VBS image C whose line-of-sight parameter is viewable from the treatment instrument 4.

Figure 19A:
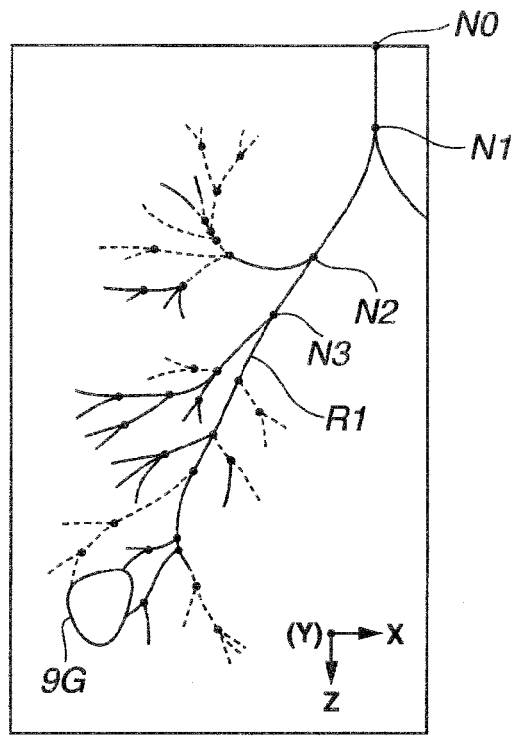
FIG. 19A is an explanatory diagram for illustrating an insertion route of the medical apparatus according to the first embodiment.
Figure 19B:
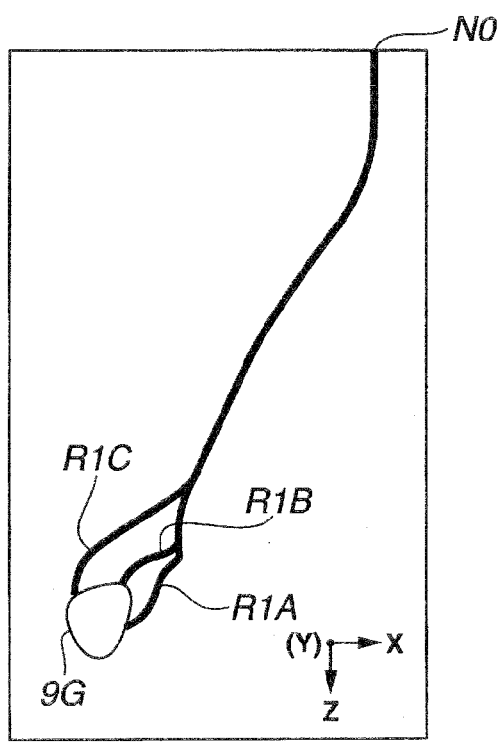
FIG. 19B is an explanatory diagram for illustrating an insertion route of the medical apparatus according to the first embodiment.

Incidentally, if, for example, there is a target site 9G of a relatively large volume at an ending of the bronchus as shown in FIG. 19A, there might be multiple insertion routes R1A, R1B, and R1C as shown in FIG. 19B. Basically, the insertion aid apparatus 3 calculates the shortest route as the insertion route.

Figure 20A:
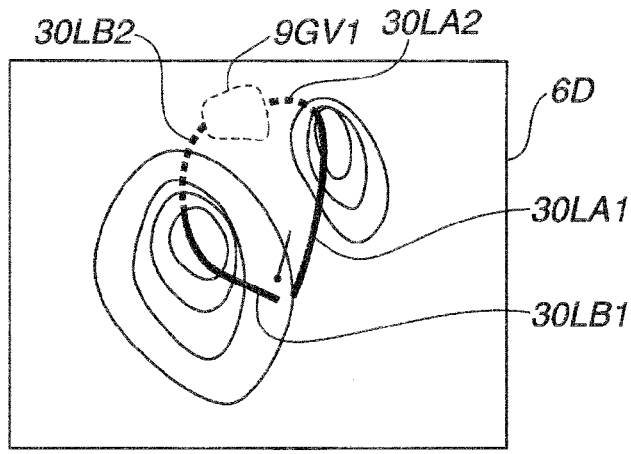
FIG. 20A is a diagram showing an example of the display screen of the medical apparatus according to the first embodiment.
Figure 20B:
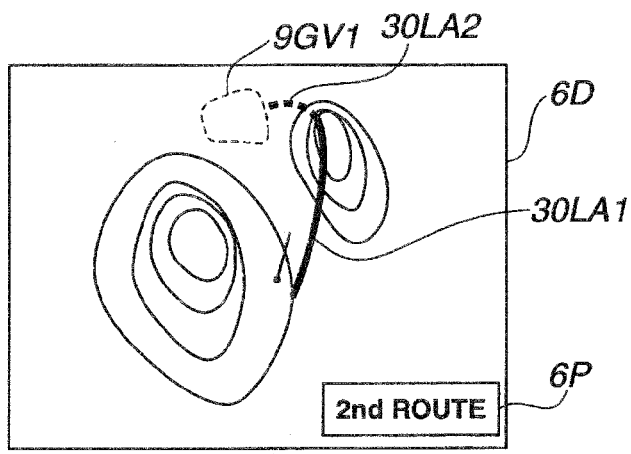
FIG. 20B is a diagram showing an example of the display screen of the medical apparatus according to the first embodiment.

However, as shown in FIG. 20A, multiple insertion routes may be displayed simultaneously when selected by the surgeon. Alternatively, as shown in FIG. 20B, by displaying the shortest insertion route first, the next shortest insertion route may be displayed when, for example, a "2nd ROUTE" (next candidate display) button 6P presented in the display unit 6 of a touch panel type is pressed or selected by an operator. Of course, the "2nd ROUTE" button may be a dedicated mechanical button. On the other hand, when multiple insertion routes are displayed simultaneously, preferably the insertion routes are displayed in different colors, line shapes, or the like.

Figure 21A:
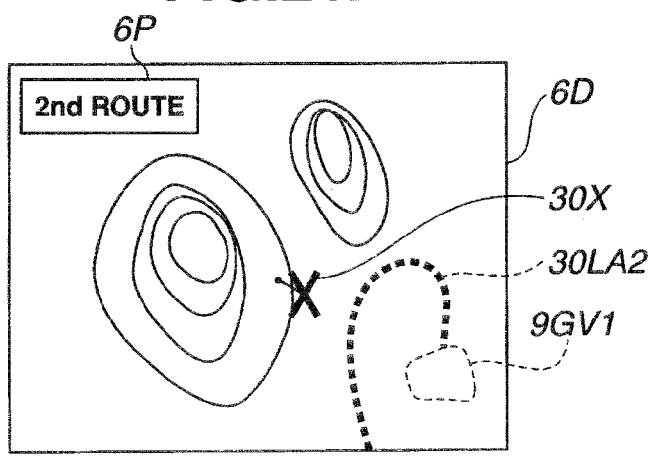
FIG. 21A is a diagram showing an example of the display screen of the medical apparatus according to the first embodiment.

As described with reference to FIG. 11, even if the distal end portion 4C is located in a lumen off the insertion route (first insertion route) due to a wrong operation, there are cases where the distal end portion 4C can reach the target site 9G through another insertion route (second insertion route). In that case, as shown in FIG. 21A, the "2nd ROUTE" button is automatically displayed in the display unit 6.

Figure 21B:
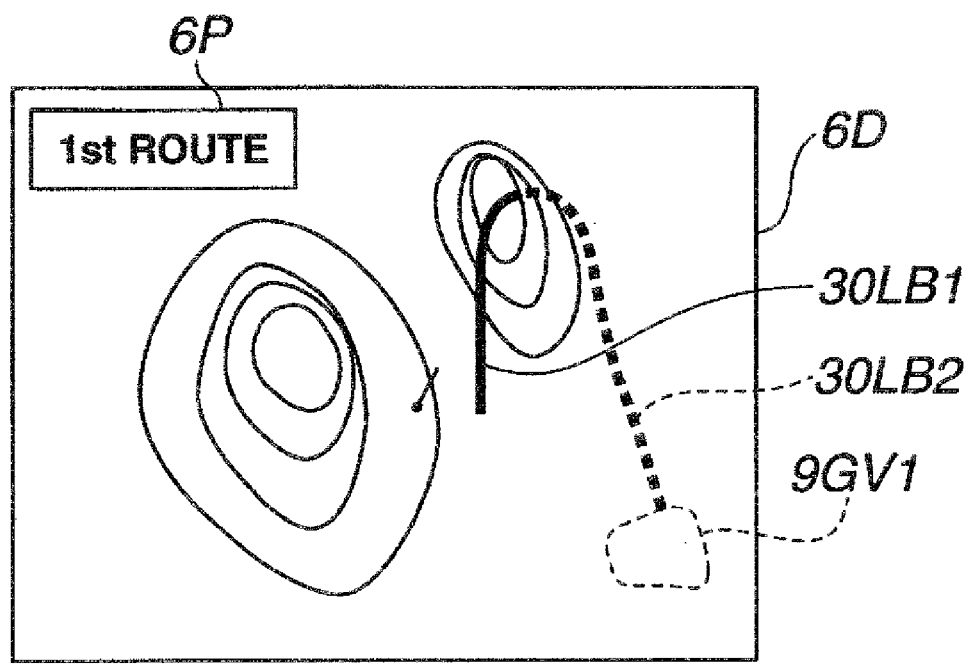
FIG. 21B is a diagram showing an example of the display screen of the medical apparatus according to the first embodiment.

As shown in FIG. 21B, when the surgeon presses the "2nd ROUTE" button, the second insertion route is displayed, allowing the surgeon to continue the insertion operation.

The insertion aid apparatus described above calculates multiple insertion routes, allowing the surgeon to select the most suitable insertion route at the time even during an insertion operation, and thus provides good operability.

Second Embodiment

Next, a medical apparatus 1A according to a second embodiment of the present invention will be described. The medical apparatus 1A according to the present embodiment is similar to the medical apparatus 1 according to the first embodiment, and the same components as those in the first embodiment are denoted by the same reference numerals as the corresponding components, and description thereof will be omitted.

Figure 22:
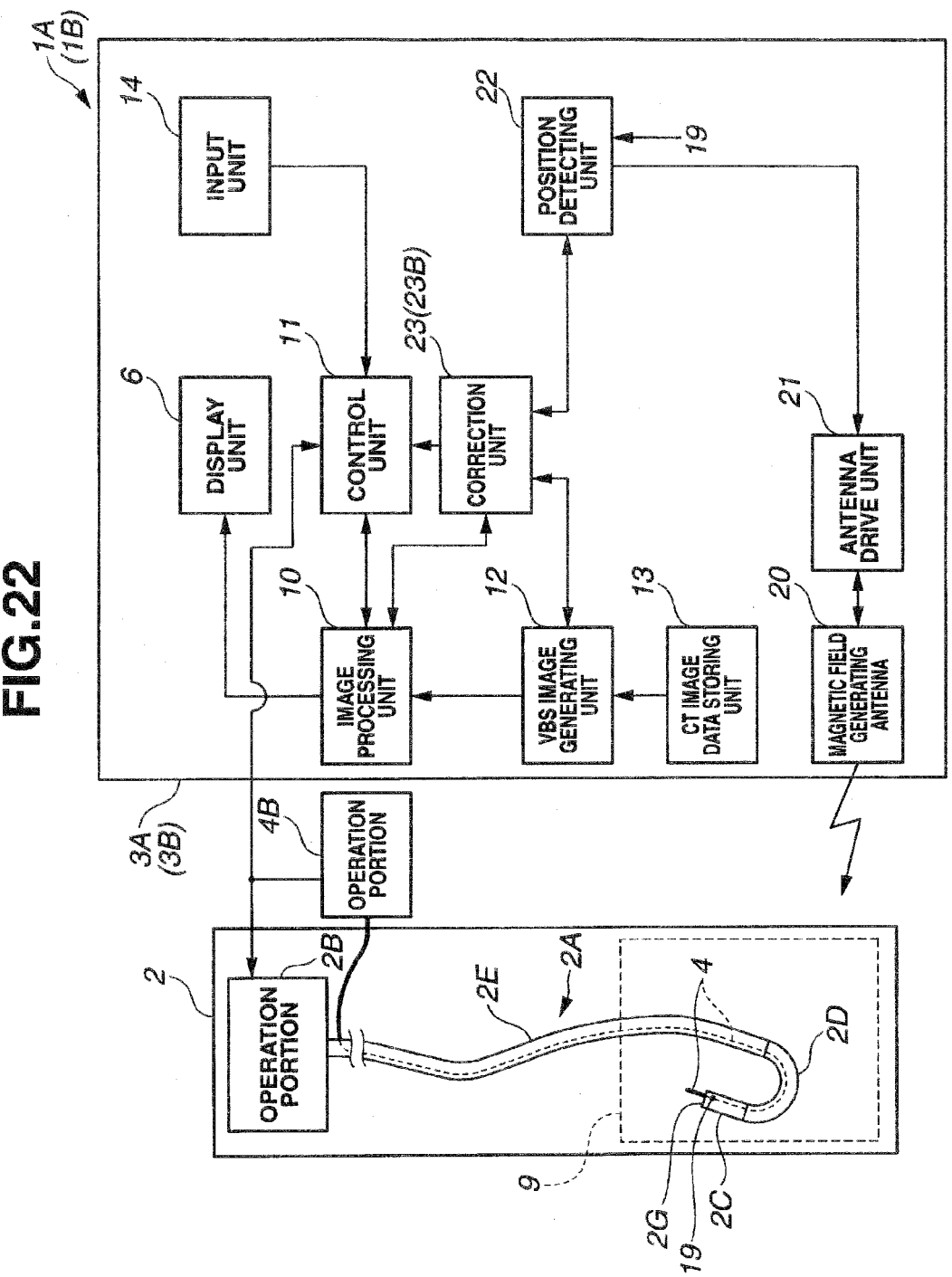
FIG. 22 is a configuration diagram for illustrating a configuration of a medical apparatus according to a second embodiment.

As shown in FIG. 22, an insertion aid apparatus 3A of the medical apparatus 1A includes a correction unit 23 adapted to correct the position and the like detected by the sensor 19, based on a real image picked up by the CCD 2G.

Figure 23:
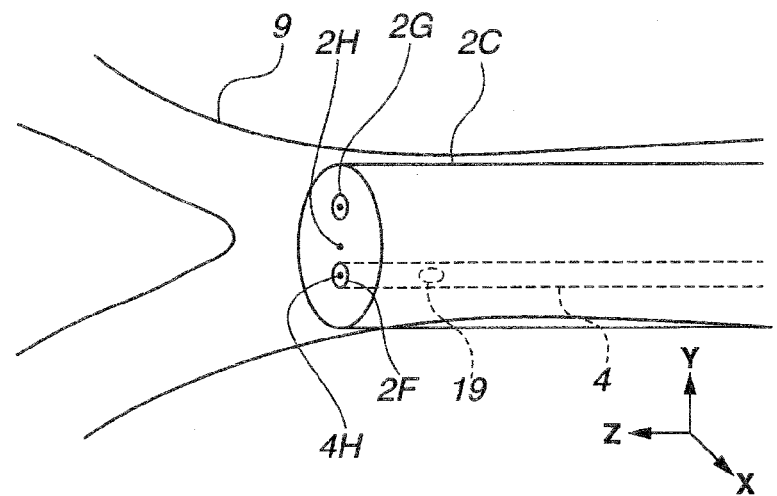
FIG. 23 is a schematic diagram for illustrating a correction method of the medical apparatus according to the second embodiment.

As shown in FIG. 23, during insertion operation of the insertion portion 2E, if the distal end 4H of the treatment instrument 4 is inserted to the position of a distal end 2H of the endoscope 2A, it is easy to know where the sensor 19 is disposed in the insertion-portion distal end portion 2C. Here, placement location of the CCD 2G in the insertion-portion distal end portion 2C is already known.

Figure 24:
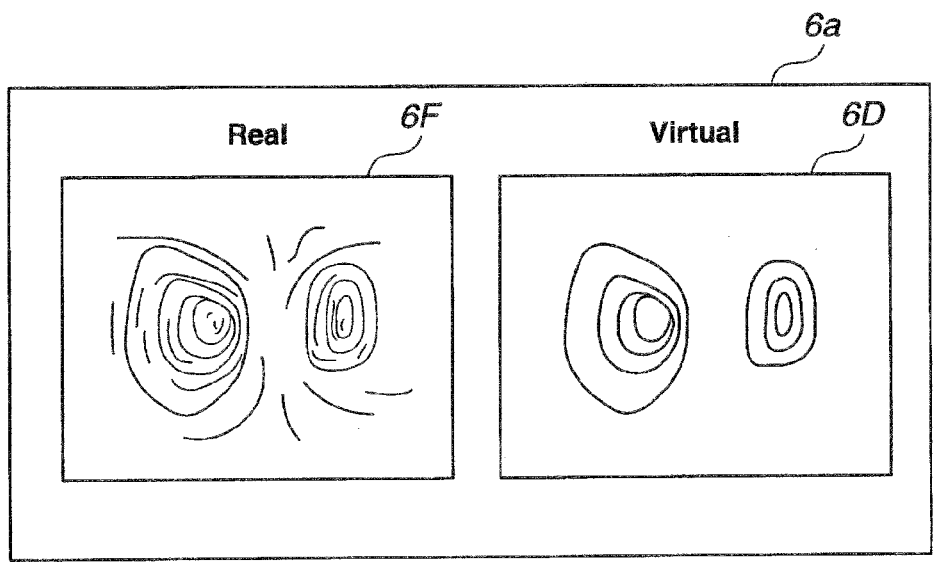
FIG. 24 is a diagram showing an example of a display screen of the medical apparatus according to the second embodiment.

On the other hand, as shown in FIG. 24, the control unit 11 can cause the VBS image generating unit 12 to generate a VBS image B similar to a real image photographed by the CCD 2G. That is, based on the position, direction, and roll angle (X0, Y0, Z0, a0, e0, r0) of the sensor 19 detected by the sensor 19, first the control unit 11 generates a VBS image B whose line-of-sight parameter includes the position, direction, and roll angle (X1, Y1, Z1, a1, e1, r1) of the CCD 2G at the time. Then, the control unit 11 compares similarity between the VBS image B and the real image. The similarity of images is checked by known image processing, which may use either matching at a pixel data level or matching at the level of features extracted from the images. The matching process of the real image and the VBS image B is performed per frame of the real image, and an actual comparison process is carried out with reference to similarity between a static endoscopic image and the VBS image B.

If the comparison and calculation of similarity between the real image and the VBS image B reveals a larger error e between the two images than an allowable error e0 (No), the control unit 11 outputs the line-of-sight parameter whose values have been changed slightly to the VBS image generating unit 12. The VBS image generating unit 12 generates a next VBS image B based on the new line-of-sight parameter.

As the insertion aid apparatus 3 repeats the above process, i.e., changes the line-of-sight parameter, the VBS image B generated by the VBS image generating unit 12 gradually becomes more similar to the real image, and after a few iterations, the error e between the two images becomes smaller than the allowable error e0.

Then, the control unit 11 detects the line-of-sight parameter of the CCD 2G, in other words, the position, direction, and roll angle (Xn, Yn, Zn, an, en, rn) of the CCD 2G, equal to or smaller than the allowable error e0 in real image information. Using the line-of-sight parameter, the correction unit 23 corrects the position, direction, and roll angle (X0, Y0, Z0, a0, e0, r0) of the sensor 19 detected by the sensor 19, based on the position, direction, and roll angle (Xn, Yn, Zn, an, en, rn) of the CCD 2G. In other words, the control unit 11 calibrates the sensor 19 based on a second virtual endoscopic image B and the real image, where the second virtual endoscopic image B has the line-of-sight parameter which is made up of the position, the direction, and the roll angle of the CCD 2G.

To carry out treatment and the like of the target site 9G, preferably the surgeon has a clearer view of a relative relationship between the distal end 4H of the treatment instrument 4 and the target site 9G. The position of the target site 9G has been set by the input unit 14 in a CT coordinate system which is based on three-dimensional image data. On the other hand, the position of the sensor 19 is obtained in a sensor coordinate system relative to, for example, the magnetic field generating antenna 20. A correction process performed by the correction unit 23 is intended not only to correct detection errors of the sensor 19, but also to ensure consistency between the CT coordinate system and the sensor coordinate system, in other words, calculate a coordinate transformation formula between the different coordinate systems. The coordinate transformation formula calculated by the correction unit 23 allows the control unit 11 to perform control more accurately and easily.

In addition to providing the advantages of the medical apparatus 1 according to the first embodiment, the medical apparatus 1A according to the present embodiment features higher processing speed and enables highly accurate navigation, and thus allows the distal end portion 4C of the treatment instrument 4 to be inserted to the target site 9G in a lumen more reliably.

Variation of Second Embodiment

Next, a medical apparatus 1B according to a variation of the second embodiment of the present invention will be described. The medical apparatus 1B according to the present variation is similar to the medical apparatus 1A according to the second embodiment, and the same components as those in the second embodiment are denoted by the same reference numerals as the corresponding components, and description thereof will be omitted.

A correction unit 23B of an insertion aid apparatus 3B of the medical apparatus 1B includes a correction unit 23B adapted to correct the position and the like detected by the sensor 19, based on an image of the treatment instrument 4 contained in a real image picked up by the CCD 12 of the endoscope 2A.

Figure 25:
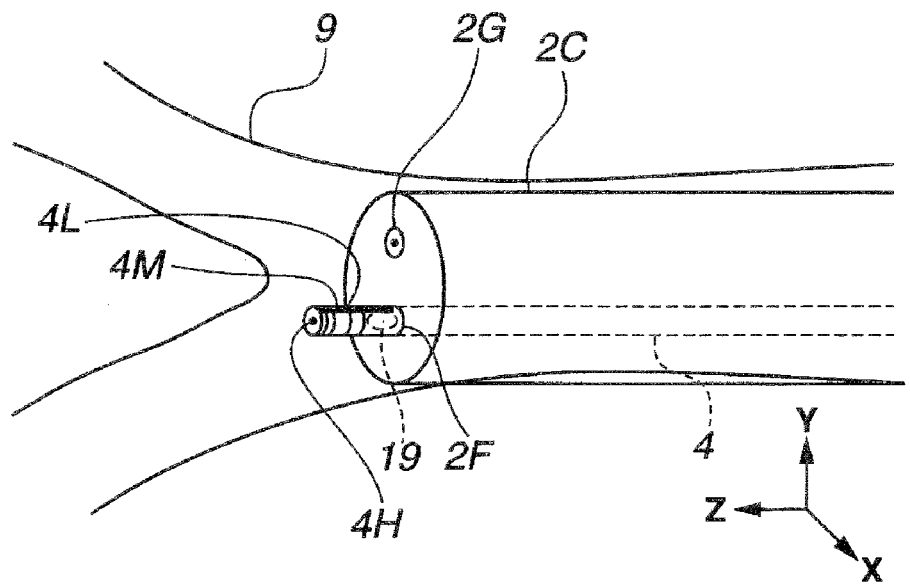
FIG. 25 is a schematic diagram for illustrating a correction method of a medical apparatus according to a variation of the second embodiment.
Figure 26:
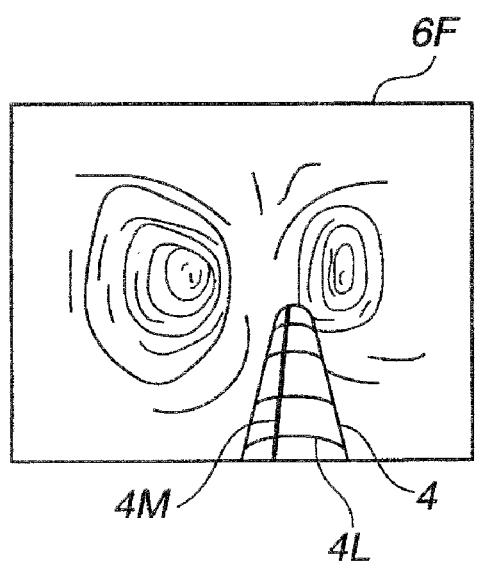
FIG. 26 is a diagram showing an example of a display screen of the medical apparatus according to the variation of the second embodiment.

That is, as shown in FIG. 25, with the medical apparatus 1B, for a correction process of the correction unit 23B, the surgeon protrudes the distal end portion 4C of the treatment instrument 4 from the treatment instrument outlet 2F of the insertion-portion distal end portion 2C. This provides a real image which shows the distal end portion 4C being picked up, as shown in FIG. 26. The treatment instrument 4 has a graduated scale 4L which allows an amount of protrusion and the like to be detected and a graduated scale 4M which allows rotation to be detected. The graduated scales can be read from the real image by the control unit 11. Based on the read data and the like, the control unit 11 can calculates a relative positional relationship between the distal end 4H of the treatment instrument 4 and the CCD 2G.

Thus, in addition to the correction process performed by the medical apparatus 1A, based on the real image which shows the distal end portion 4C being picked up, the control unit 11 corrects the information detected by the sensor 19 to improve accuracy of the information, and in other words, calibrates the information from the sensor 19.

In addition to providing the advantages of the medical apparatus 1A according to the second embodiment, the medical apparatus 1B according to the present embodiment enables more accurate navigation, and thus allows the distal end portion 4C of the treatment instrument 4 to be inserted to the target site 9G in a lumen more reliably.

Third Embodiment

A medical apparatus 1C according to a third embodiment is similar to the medical apparatus 1 according to the first embodiment, and the same components as those in the first embodiment are denoted by the same reference numerals as the corresponding components, and description thereof will be omitted.

As shown in FIG. 27, the medical apparatus 1C according to the present embodiment includes a treatment instrument 4 inserted alone into the bronchus 9 of the patient and a reference marker 24 placed on a body surface of the patient 7. By obtaining position of the reference marker 24 in the sensor coordinate system relative to the magnetic field generating antenna 20, the medical apparatus 1C can ensure consistency between the CT coordinate system and the sensor coordinate system, and in other words, calculate a coordinate transformation formula between the different coordinate systems.

With the medical apparatus 1C, the treatment instrument 4 cannot acquire endoscopic images of bifurcations during insertion operation. However, the surgeon can insert the distal end portion 4C to the target site 9G based on the VBS image A and operations guide image 30 displayed by an insertion aid apparatus 3C of the medical apparatus 1C.

Movements of the insertion aid apparatus 3 of the medical apparatus 1C are the same as movements carried out to aid the treatment instrument 4 in the medical apparatus 1.

The medical apparatus 1C according to the present embodiment provides the same advantages as the medical apparatus 1 according to the first embodiment.

As described above, the medical apparatus according to the present invention includes: a treatment instrument inserted in a channel of an endoscope so as to protrude from an endoscopic distal end portion, equipped with a sensor and a bending portion in a distal end portion, and inserted to a target site in a bronchus, where the sensor is intended to detect a position, a direction, and a roll angle; an image data storing unit adapted to store three-dimensional image data of the bronchus acquired in advance; an input unit used to set the target site; a virtual endoscopic image generating unit adapted to generate a virtual endoscopic image using a line-of-sight parameter which includes the position, the direction, and the roll angle of the distal end portion detected by the sensor, based on the three-dimensional image data; an image processing unit adapted to perform a superimposition process and thereby display bending operation information of the bending portion, rotating operation information of the distal end portion, the virtual endoscopic image, and an insertion route in superimposition with one another to help insert the distal end portion to the target site through the bronchus.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical apparatus comprising:
   an endoscopic insertion portion provided with an image pickup unit and a channel which passes through an inner part;
   a treatment unit provided with a sensor and a bending portion and passed through the channel, with a distal end portion of the treatment unit being allowed to protrude from an insertion-portion distal end portion of the endoscopic insertion portion, where the sensor is disposed in the distal end portion and configured to detect a position, a direction, and a roll angle and the bending portion is adapted to bend the distal end portion;
   a storage unit adapted to store three-dimensional image data of the lumen of a subject acquired in advance;
   a target position setting unit adapted to set the target position based on the three-dimensional image data;
   a virtual endoscopic image generating unit adapted to generate a virtual endoscopic image using a line-of-sight parameter which includes the position, the direction, and the roll angle of the distal end portion detected by the sensor, based on the three-dimensional image data; and
   an image processing unit adapted to perform a superimposition process and thereby display operation information used to insert the distal end portion to the target position in superimposition on the virtual endoscopic image.

2. The medical apparatus according to claim 1, wherein:
   the bending portion is bendable in an up/down direction or a left/right direction; and
   the operation information processed by the image processing unit is information about a bending angle of the bending portion and a roll angle of the distal end portion.

3. The medical apparatus according to claim 1, wherein the lumen has a plurality of bifurcations.

4. The medical apparatus according to claim 1, wherein the image processing unit further performs a superimposition process of an insertion route used to insert the distal end portion to the predetermined position.

5. The medical apparatus according to claim 4, wherein when there are a plurality of the insertion routes, the image processing unit performs a superimposition process and thereby displays all of the plurality of insertion routes or a selected one of the insertion routes.

6. The medical apparatus according to claim 4, wherein:
   the target position setting unit is able to set a target site having a predetermined volume as the target position;
   the image processing unit performs a superimposition process and thereby displays the predetermined volume of the target site, a length of the insertion route from the distal end portion to the target site, and a number of bifurcations on the insertion route from the distal end portion to the target site in superimposition with one another.

7. The medical apparatus according to claim 1, further comprising a correction unit adapted to correct a position, a direction, and a roll angle detected by the sensor based on an endoscopic image picked up by the image pickup unit and a second virtual endoscopic image having a line-of-sight parameter which includes a position, a direction, and a roll angle of the image pickup unit and calculate a coordinate transformation formula used to transform coordinates of the position detected by the sensor into a coordinate system of the three-dimensional image data.

8. The medical apparatus according to claim 7, wherein the endoscopic image is an image with the distal end portion protruding from the insertion-portion distal end portion picked up.

9. The medical apparatus according to claim 7, wherein a position of the distal end portion of the treatment unit protruding from the insertion-portion distal end portion is located in a place into which the insertion-portion distal end portion is not insertable.

10. The medical apparatus according to claim 1, wherein the lumen is a bronchus.

11. The medical apparatus according to claim 1, wherein the image processing unit performs a superimposition process and thereby displays the operation information when at least one of a bending operation of the bending portion and a rotating operation of the distal end portion is necessary.

12. The medical apparatus according to claim 11, wherein the image processing unit determines whether or not the bending operation or the rotating operation is necessary by comparing the bending angle and the roll angle which provide the operation information with respective predetermined thresholds.

13. The medical apparatus according to claim 1, wherein the operation information processed by the image processing unit is displayed graphically.

* * * * *